United States Patent [19]

Jarmell et al.

[11] 4,303,615
[45] Dec. 1, 1981

[54] CRUCIBLE WITH LID

[75] Inventors: Solomon Jarmell, Pittsburgh; Barry E. Rodgers, Eastmont, both of Pa.

[73] Assignee: Fisher Scientific Company, Pittsburgh, Pa.

[21] Appl. No.: 155,662

[22] Filed: Jun. 2, 1980

[51] Int. Cl.³ ........................ B01L 3/04; G01N 25/00
[52] U.S. Cl. ................................... 422/102; 215/307; 422/78; 432/262
[58] Field of Search .......................... 422/102, 242, 78; 23/230 PC; 432/262, 263, 264, 265; 215/307

[56] References Cited

U.S. PATENT DOCUMENTS

| | | | |
|---|---|---|---|
| 290,900 | 12/1883 | Mallory | 215/307 |
| T921,006 | 4/1974 | Wimberley | 422/102 X |
| 1,609,096 | 11/1926 | Smith | 432/262 |
| 1,720,327 | 7/1929 | Halvorson | |

FOREIGN PATENT DOCUMENTS

14242 of 1904 United Kingdom ................. 432/262

OTHER PUBLICATIONS

Thermal American Fused Quartz Company, "TAFQ-"—Catalog, p. 19.
Draft ISO Recommendation No. 550, "Determination of the Volatile Matter of Hard Coal and of Coke."
Aloe Scientific, "Laboratory Apparatus—Equipment—Reagents for the Chemical and Biological Sciences—Catalog No. 103, 1952, pp. 314-317.

*Primary Examiner*—Arnold Turk
*Attorney, Agent, or Firm*—Webb, Burden, Robinson & Webb

[57] ABSTRACT

A self-sealing ceramic crucible and lid combination suitable for proximate analysis of coal or coke samples. The combination comprises a generally cylindrical crucible vessel having a substantially flat outside bottom surface one one end and being open on the other end, the wall of the vessel terminating at its open end in a rim which is finished circumferentially for sealing with the lid. The inside bottom surface is also preferably substantially flat. The lid member is generally cup-shaped and has a circular top wall and a depending circumferential skirt portion, the upper surface of the top wall being generally flat, the inside diameter of the top wall being slightly greater than the outside diameter of the crucible vessel, such that when the lid member is placed on the crucible vessel, the lower surface of the top wall which has a finished annular recess rests on the rim of the crucible, and the skirt of the lid member extends downwardy along the wall of the crucible and terminates in a circular edge. The finished annular recess in the lower surface of the top wall of the lid member is located adjacent the depending skirt portion, whereby a seal is effected between the crucible and the lid by gravity engagement of the finished rim of the crucible with the finished annular recess of the lid to prevent air from entering the crucible during a volatile run, but permitting gases to be expelled from the crucible during the burn-off period without ashing the sample in the volatile portion of the analysis. The combination allows a complete proximate analysis to be run on a single sample. Preferably, the crucible and lid are made from vitreous silica and finishing is done by grinding.

4 Claims, 3 Drawing Figures

CRUCIBLE WITH LID

BACKGROUND OF THE INVENTION

1. Field of the Invention

This invention relates to crucibles and particularly to crucibles for use in chemical analysis, such as coal and coke analysis.

2. Description of the Prior Art

To predict the behavior of coal in a furnace, certain tests have been developed and procedures called proximate analysis have been established by ASTM for quantitatively determining the percentage of moisture, ash and volatile matter in a coal sample. The percentage of fixed carbon in the sample can then be calculated as the difference. The ASTM testing procedures are prescribed in ASTM D3173-73 (Reapproved 1979), D3174-73 (Reapproved 1979), D3175-77 and D3172-73 (Reapproved 1979).

These tests require that the samples be loaded in crucibles for weighing and for heating in a laboratory furnace. Various types of crucibles have been proposed for use in coal and coke analysis such as those disclosed, for example, in U.S. Pat Nos. 1,609,096 and 1,720,327. Prior crucibles have not been entirely satisfactory, however, since they did not have a cooperating lid which would properly seal to exclude air and release volatiles from the crucible as required during testing.

SUMMARY OF THE INVENTION

We have invented an improved self-sealing ceramic crucible and lid especially for use in proximate analysis of coal and coke. The crucible is a generally cylindrical vessel having substantially flat inside and outside bottom surfaces on one end and being open on the other end. The wall of the cylindrial vessel terminates at its open end in a rim which is finished circumferentially for sealing with the lid. Preferably, the crucible is made of vitreous silica and particularly of quartz which is water-free. Suitable materials are General Electric Company Type 204 clear fused quartz tubing or Vitreosil clear fused quartz.

The lid for the crucible is a generally cup-shaped member having a circular top wall and a depending circumferential skirt portion. The upper surface of the top wall is generally flat. The inside diameter of the top wall is slightly greater than the outside diameter of the crucible with which it is to be used such that when the lid is placed on the crucible, the lower surface of the top wall of the lid which has a finished annular recess rests on the rim of the crucible, and the skirt of the lid extends downwardly along the wall of the crucible and terminates in a circular edge. The finished annular recess is provided in the lower surface of the top wall of the lid adjacent the depending skirt. The seal between the crucible and lid is effected by gravity engagement of the finished rim of the crucible with the finished annular recess of the lid to prevent air from entering the crucible during a volatile run and contaminating a sample during analysis. Since the lid is not secured to the crucible except by gravity, upon heating of the crucible, as for example, in proximate analysis of coal or coke, gases can be expelled from the crucible during the burn-off period without admitting air past the seal and ashing the sample.

The crucible and lid combination of the present invention provides the advantages of a stable flat surfaced vessel for use in chemical analysis, an airtight self-seal between the lid and crucible and eliminates the possibility of the lid being separated from the crucible either accidentally or during heating of the crucible. The combination allows a complete analysis to be run on a single sample.

In laboratory tests we have found that the dimensions of the crucible and lid are particularly important and that a crucible and lid having the dimensions described in the specific example given hereinafter provide optimum results in doing proximate analysis.

DETAILED DESCRIPTION OF A PREFERRED EMBODIMENT OF THE INVENTION

Figure 1:
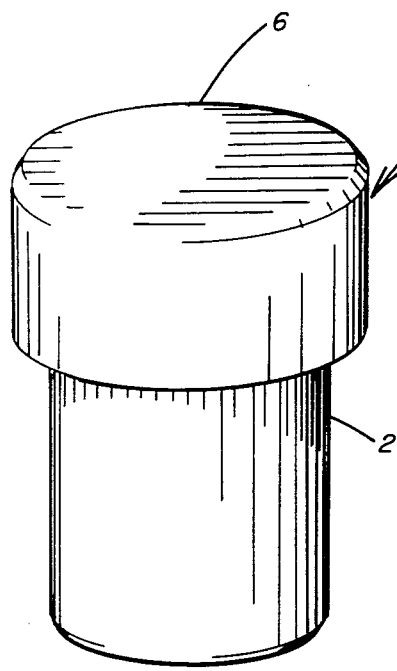
FIG. 1 is an elevational view of the crucible and lid in accordance with the invention.

Referring to the drawings, a quartz crucible 1 comprises a generally cylindrical vessel having a sidewall 2 and a bottom wall 3. The inside and outside surfaces of the bottom wall are preferably substantially flat to provide stability to the crucible and for uniform heat transfer to a sample in the crucible. The opposite end of the vessel from the bottom wall 3 is open. The sidewall 2 of the crucible terminates at the open end in a finished rim 4, having a circumference 5 made by grinding the quartz on the outside edge of the rim 4. The rim 4 is thus adapted to engage a lid 6 in sealing contact.

The lid 6 of the crucible is a generally cup-shaped member having a circular top wall 7 and a depending circumferential skirt 8 which terminates in an edge 9, which is preferably fire-polished. The upper surface of the top wall is generally flat. The lower surface of the top wall 7 has an inside diameter which is slightly greater than the outside diameter of the crucible with which it is to be used such that when the lid 6 is to be placed on the crucible 1, the lower surface of the top wall which includes a finished annular recess 10 rests on the rim 4 of the crucible, and the skirt 8 extends downwardly along the sidewall of the crucible, as more particularly shown in FIG. 2.

Figure 2:
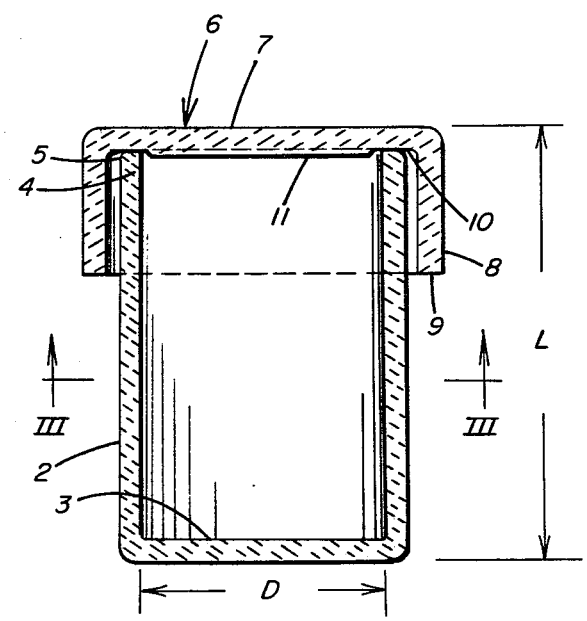
FIG. 2 is a sectional view taken on a vertical plane through the center of the crucible and lid shown in FIG. 1.
Figure 3:
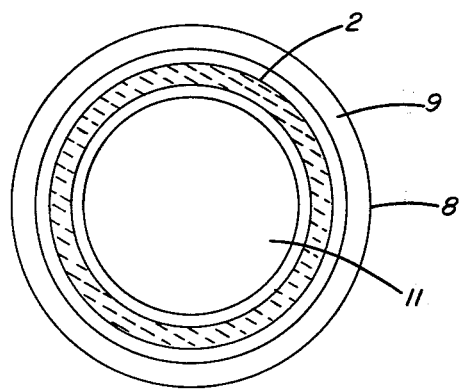
FIG. 3 is a sectional view taken along lines III—III of FIG. 2.

The finished annular recess 10 is provided by grinding the lower surface of the top wall of the lid adjacent the skirt 8. When the lid is placed on the crucible, as shown in FIG. 2, a seal is effected between the finished rim 4 of the crucible with the finished annular recess 10 of the lid by gravity to prevent air from entering the crucible during analysis. Upon heating, however, the seal is broken to permit volatiles to be driven off without exposing the sample to air and ashing it. In burning a sample to ash, as in proximate analysis, the lid is removed entirely to admit air.

The seal between the crucible and lid is made by engagement of the ground quartz of the crucible with the ground annular recess in the lower surface of the lid. The central portion 11 of the bottom surface thus extends into the open end of the crucible, providing a stable crucible and lid combination wherein the lid is not easily accidentally separated from the crucible, voiding the integrity of the analysis being conducted.

EXAMPLE

For proximate analysis of a coal or coke sample it is essential that the dimensions of the crucible be selected to insure that a seal between the crucible and lid is made by gravity to prevent air from being admitted to the crucible, yet permit the seal to be broken when the sample is heated to drive off volatiles from the sample. Accordingly, we have identified optimum dimensions for a crucible and lid combination for use in proximate analysis and we have successfully used such combination in the laboratory in actual testing. The following example describes the crucible and lid which we have found to be the best embodiment of our invention; all dimensions are given in millimeters (mm) and the letters given in parentheses refer to FIG. 2.

The total length (L) of the crucible 1 is 34 mm and the outside diameter is 22.5 mm ($\pm 0.5$ mm). The thickness of the bottom wall 3 is 1.5 mm. The inside diameter (D) of the crucible is 20 mm. We have found that the ratio of L/D should be less than or equal to 2 for optimum results in proximate analysis.

The lid 6 for this crucible has an outside diameter of 27 mm ($\pm 1.1$ mm). The thickness of the central portion 11 of the top wall 7 is 2 mm and the length of the skirt (measured from the upper surface of the top wall to edge 9 of the skirt) is 12 mm ($\pm 1$ mm). The inside diameter of the lid is 24 mm ($\pm 0.5$, $-0$ mm).

We have found that a crucible and lid combination having these dimensions is especially satisfactory for purposes of proximate analysis, although minor changes may be made without adversely affecting performance of the combination in laboratory analysis.

Having described a presently prefered embodiment of the invention, it is to be understood that it may be otherwise embodied within the scope of the appended claim.

We claim:

1. A self-sealing ceramic crucible and lid combination suitable for proximate analysis of coal or coke samples comprising:
   A. a generally cylindrical crucible vessel having a substantially flat outside bottom surface on one end and being open on the other end, the wall of the vessel terminating at its open end in a rim which is circumferentially finished for sealing with the lid; and
   B. a generally cup-shaped lid member having a circular top wall and a depending circumferential skirt portion which terminates in a circular edge, the upper surface of the top wall being generally flat, the lower surface of the top wall including a finished annular recess adjacent the depending skirt portion, the inside diameter of the top wall being slightly greater than the outside diameter of the crucible vessel such that when the lid member is placed on the crucible vessel the annular recess in the lower surface of the top wall rests on the finished rim of the crucible and the skirt of the lid member extends downwardly along the wall of the crucible, whereby a seal is effected by gravity engagement of the finished rim of the crucible with the finished annular recess of the lid to prevent air from entering the crucible during a volatile run, but permitting gases to be expelled from the crucible during the burn-off period without ashing the sample in the volatile portion of proximate analysis.

2. The combination as set forth in claim 1 wherein the ceramic is a vitreous silica material.

3. The combination as set forth in claim 1 or claim 2 wherein the ceramic is a water-free quartz material.

4. The combination as set forth in claim 1 or claim 2 wherein the ratio of the length (L) to the inside diameter (D) of the crucible is less than or equal to 2.

* * * * *